United States Patent [19]

Ting et al.

[11] Patent Number: 5,994,505
[45] Date of Patent: Nov. 30, 1999

[54] FORMS OF CLASS II MHC TRANSACTIVATOR (CIITA)

[75] Inventors: Jenny Pan-Yung Ting; Keh-Chuang Chin, both of Chapel Hill, N.C.

[73] Assignee: The University of North Carolina at Chapel Hill, Chapel Hill, N.C.

[21] Appl. No.: 08/988,128

[22] Filed: Dec. 10, 1997

Related U.S. Application Data

[60] Provisional application No. 60/035,264, Dec. 11, 1996.

[51] Int. Cl.⁶ .................................................. C07K 14/00
[52] U.S. Cl. ............................................................ 530/350
[58] Field of Search ................................... 530/350, 358; 536/23.5

[56] References Cited

U.S. PATENT DOCUMENTS 5,672,473  9/1997  Glimcher et al. ........................... 435/6

FOREIGN PATENT DOCUMENTS

WO96/06107  2/1996  WIPO .

OTHER PUBLICATIONS

Brown et al.; Characterization Of The Expressed CIITA Allele In The Class II MHC Transcriptional Mutant RJ2.2.5., *Immunogenetics*, 43:88–91 (1995).

Lemon et al.; The RAG cell line defines a new complementation group of MHC class II deficiency, *Immunogenetics*, 43:352–359 (1996).

International Search Report mailed Apr. 13, 1998.

Riley, R.L. et al. Immunity. vol. 2, pp. 533–543, 1995.

Steimle, V. et al. Cell. vol. 75, pp. 135–146, Oct. 8, 1993.

Mach, B. et al. Annual Review of Immunology, vol. 14, pp. 301–331. Paul, Fathman and Metzger, eds. Annual Reviews, Inc. Palo Alto, 1996.

*Primary Examiner*—James Ketter
*Assistant Examiner*—Irem Yucel
*Attorney, Agent, or Firm*—Myers Bigel Sibley & Sajovec, P.A.

[57] ABSTRACT

Novel deletion mutants of the class II transactivator protein (CIITA) are disclosed. Isolated DNA encoding such mutants are also disclosed, as are recombinant DNA vectors containing said DNA, and antibodies that specifically bind the mutant CIITA proteins. Additionally, methods of treating disorders characterized by abnormal expression of major histocompatibility complex (MHC) antigens by administering novel mutants of the present invention are also disclosed.

1 Claim, 4 Drawing Sheets

FIG. 1

| Lanes | Constructs | | Relative CAT Activity |
|---|---|---|---|
| 1 | pcDNA3 | | 0.16 |
| 2 | FLAG.CIITA | 1 A P S T    BLS-2A    1130 | 1.00 |
| 3 | CIITA(Δ132-301) | | 0.15 |
| 4 | CIITA(Δ132-212) | | 1.16 |
| 5 | CIITA(Δ209-301) | | 1.22 |

FIG. 2A

GTPase consensus motifs: GXXXXGKS/T..(35-263)..DXXG..(50-67)..N/TKXD

CIITA: $^{421}$GKAGQGKS.....(33).........DAYG..(93).........SKAD$^{561}$

RAS: $^{5}$GAGGVGKS.....(41).........DTAG..(45).........NKCD$^{119}$

FIG. 2B

| | |
|---|---|
| FLAG.CIITA | GKAGQGKS.....(33).........DAYG..(93).........SKAD |
| CIITA-GTP1(ΔGK) | XXAGQGKS.....(33).........DAYG..(93).........SKAD |
| CIITA-GTP1(K→E) | GKAGQGES.....(33).........DAYG..(93).........SKAD |
| CIITA-GTP2(ΔDAYG) | GKAGQGKS.....(33).........XXXX..(93).........SKAD |
| CIITA-GTP3(ΔSKAD) | GKAGQGKS.....(33).........DAYG..(93).........XXXX |

FIG. 3

| Lanes | Constructs | | Relative CAT Activity |
|---|---|---|---|
| 1 | pcDNA3 | | 0.16 |
| 2 | FLAG.CIITA | GKAGQGKS......(33).........DAYG..(93).........SKAD | 1.00 |
| 3 | CIITA-GTP1(ΔGK) | XXAGQGKS......(33).........DAYG..(93).........SKAD | 0.38 |
| 4 | CIITA-GTP1(K→E) | GKAGQGES......(33).........DAYG..(93).........SKAD | 0.30 |
| 5 | CIITA-GTP2(ΔDAYG) | GKAGQGKS......(33).........XXXX..(93).........SKAD | 0.10 |
| 6 | CIITA-GTP3(ΔSKAD) | GKAGQGKS......(33).........DAYG..(93).........XXXX | 0.20 |

FIG. 4

| Lanes | Constructs | | Relative CAT Activity |
|---|---|---|---|
| 1 | pcDNA3 | | 0.15 |
| 2 | FLAG.CIITA | 1 A P S T — BLS-2Δ — 1130 | 1.00 |
| 3 | CIITA(1-931) | 931 | 0.16 |
| 4 | CIITA(1-949) | 949 | 0.24 |
| 5 | CIITA(1-1017) | 1017 | 0.25 |
| 6 | CIITA(1-1059) | 1059 | 0.13 |
| 7 | CIITA(1-1089) | 1089 | 0.12 |

SEQUENCE LISTING (1) GENERAL INFORMATION:

(iii) NUMBER OF SEQUENCES: 18

(2) INFORMATION FOR SEQ ID NO:1:

(i) SEQUENCE CHARACTERISTICS:
      (A) LENGTH: 88 base pairs
      (B) TYPE: nucleic acid
      (C) STRANDEDNESS: single
      (D) TOPOLOGY: linear    (ii) MOLECULE TYPE: DNA (genomic)

(xi) SEQUENCE DESCRIPTION: SEQ ID NO:1:

CCGGAATTCA TGGACTACAA AGACGATGAC GATAAAATGC GTTGCCTGGC TCCACGCCCT    60

GCTGGGTCCT ACCTGTCAGA GCCCCAAG    88

(2) INFORMATION FOR SEQ ID NO:2:

(i) SEQUENCE CHARACTERISTICS:
      (A) LENGTH: 88 base pairs
      (B) TYPE: nucleic acid
      (C) STRANDEDNESS: single
      (D) TOPOLOGY: linear    (ii) MOLECULE TYPE: DNA (genomic)

(xi) SEQUENCE DESCRIPTION: SEQ ID NO:2:

CCGGAATTCA TGGACTACAA AGACGATGAC GATAAAATGC GTTGCCTGGC TCCACGCCCT    60

GCTGGGTCCT ACCTGTCAGA GCCCCAAG    88

(2) INFORMATION FOR SEQ ID NO:3:

(i) SEQUENCE CHARACTERISTICS:
      (A) LENGTH: 29 base pairs
      (B) TYPE: nucleic acid
      (C) STRANDEDNESS: single
      (D) TOPOLOGY: linear    (ii) MOLECULE TYPE: DNA (genomic)

(xi) SEQUENCE DESCRIPTION: SEQ ID NO:3:

AAATGCTTCA ATGCTAGCGA AAAAGGAAG    29

(2) INFORMATION FOR SEQ ID NO:4:

(i) SEQUENCE CHARACTERISTICS:
      (A) LENGTH: 40 base pairs
      (B) TYPE: nucleic acid
      (C) STRANDEDNESS: single
      (D) TOPOLOGY: linear    (ii) MOLECULE TYPE: DNA (genomic)

(xi) SEQUENCE DESCRIPTION: SEQ ID NO:4:

GCCCAACTTC TGCTGGCATA TCGATACTCT CACCGATCAC    40

(2) INFORMATION FOR SEQ ID NO:5:

(i) SEQUENCE CHARACTERISTICS:
        (A) LENGTH: 39 base pairs
        (B) TYPE: nucleic acid
        (C) STRANDEDNESS: single
        (D) TOPOLOGY: linear     (ii) MOLECULE TYPE: DNA (genomic)

(xi) SEQUENCE DESCRIPTION: SEQ ID NO:5:

GAGGTCAGGG CAGGTTCATC GATGCTGGGC AGGTCAGTG                          39

(2) INFORMATION FOR SEQ ID NO:6:

(i) SEQUENCE CHARACTERISTICS:
        (A) LENGTH: 40 base pairs
        (B) TYPE: nucleic acid
        (C) STRANDEDNESS: single
        (D) TOPOLOGY: linear     (ii) MOLECULE TYPE: DNA (genomic)

(xi) SEQUENCE DESCRIPTION: SEQ ID NO:6:

GCCCAACTTC TGCTGGCATA TCGATACTCT CACCGATCAC                         40

(2) INFORMATION FOR SEQ ID NO:7:

(i) SEQUENCE CHARACTERISTICS:
        (A) LENGTH: 43 base pairs
        (B) TYPE: nucleic acid
        (C) STRANDEDNESS: single
        (D) TOPOLOGY: linear     (ii) MOLECULE TYPE: DNA (genomic)

(xi) SEQUENCE DESCRIPTION: SEQ ID NO:7:

CAACGAGGAA CTGGAGAAAT CGATGGGAAT CTGGTCGGTT TTC                    43

(2) INFORMATION FOR SEQ ID NO:8:

(i) SEQUENCE CHARACTERISTICS:
        (A) LENGTH: 43 base pairs
        (B) TYPE: nucleic acid
        (C) STRANDEDNESS: single
        (D) TOPOLOGY: linear     (ii) MOLECULE TYPE: DNA (genomic)

(xi) SEQUENCE DESCRIPTION: SEQ ID NO:8:

CAACGAGGAA CTGGAGAAAT CGATGGGAAT CTGGTCGGTT TTC                    43

(2) INFORMATION FOR SEQ ID NO:9:

(i) SEQUENCE CHARACTERISTICS:
        (A) LENGTH: 39 base pairs
        (B) TYPE: nucleic acid
        (C) STRANDEDNESS: single
        (D) TOPOLOGY: linear     (ii) MOLECULE TYPE: DNA (genomic)

(xi) SEQUENCE DESCRIPTION: SEQ ID NO:9:

GAGGTCAGGG CAGGTTCATC GATGCTGGGC AGGTCAGTG                          39

(2) INFORMATION FOR SEQ ID NO:10:

(i) SEQUENCE CHARACTERISTICS:
        (A) LENGTH: 34 base pairs (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:10:

CTCTTGCCCT GACCAGCCAC AGCAATCACT CGTG                                        34

(2) INFORMATION FOR SEQ ID NO:11:

(i) SEQUENCE CHARACTERISTICS:
        (A) LENGTH: 36 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:11:

CCCAGCCCAA TAGCTCTCGC CCTGACCAGC TTTGCC                                      36

(2) INFORMATION FOR SEQ ID NO:12:

(i) SEQUENCE CHARACTERISTICS:
        (A) LENGTH: 31 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:12:

GAGCAGATCC TGCAGCCCCG GACGGTTCAA G                                           31

(2) INFORMATION FOR SEQ ID NO:13:

(i) SEQUENCE CHARACTERISTICS:
        (A) LENGTH: 30 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:13:

CAGCTCAAAT AGGGCCAGGC TCTGGACCAG                                             30

(2) INFORMATION FOR SEQ ID NO:14:

(i) SEQUENCE CHARACTERISTICS:
        (A) LENGTH: 33 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:14:

GTCTGCACAA GCTTTCACAA ATCTTCCACA TCC                                         33

(2) INFORMATION FOR SEQ ID NO:15:

(i) SEQUENCE CHARACTERISTICS:
        (A) LENGTH: 34 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:15:

CGAACAGCAG GGAGCTACCC AGCTGTGTCT TCCG                    34

(2) INFORMATION FOR SEQ ID NO:16:

(i) SEQUENCE CHARACTERISTICS:
        (A) LENGTH: 24 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:16:

CAGCGAGCTG CTAGGCCCCG GCAG                               24

(2) INFORMATION FOR SEQ ID NO:17:

(i) SEQUENCE CHARACTERISTICS:
        (A) LENGTH: 28 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:17:

CAAGCTCTCG GCTCACACGT CGCAGATG                           28

(2) INFORMATION FOR SEQ ID NO:18:

(i) SEQUENCE CHARACTERISTICS:
        (A) LENGTH: 25 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:18:

GATTGAGGGT TACAAGGACT TCAGC                              25

FORMS OF CLASS II MHC TRANSACTIVATOR (CIITA)

RELATED APPLICATIONS

This application claims the benefit of U.S. Provisional Application Ser. No. 60/035,264, filed Dec. 11, 1996.

STATEMENT OF FEDERAL SUPPORT

This invention was made with Government support under grant CA48185 from the National Institutes of Health (NIH). The Government has certain rights to this invention.

FIELD OF THE INVENTION

The present invention relates to transcription factors that regulate major histocompatibility (MHC) gene expression, and more specifically relates to class II transactivators (CIITA) and mutants thereof.

BACKGROUND OF THE INVENTION

The major histocompatibility complex (MHC) gene products play a critical role in regulating the cellular immune response. In particular, the appropriate constitutive and inducible expression of class II MHC molecules is essential for normal immune response, whereas aberrantly high or low expression has been correlated with various autoimmune diseases (P. T. Massa et al., *Proc. Natl. Acad. Sci. USA* 84, 4219–4223 (1987)) and a type of severe combined immunodeficiency diseases (SCID) known as the Bare Lymphocyte Syndrome (BLS) (C. Griscelli et al., *Immunodeficiency Rev.* 1, 135–53 (1989)). Additionally, the class II major histocompatibility (MHC) antigens are known to play a crucial role in causing organ transplant rejections.

The primary regulation of both constitutive and IFN-γ-induced class II MHC genes occurs at the transcriptional level. F. Figueiredo et al., *J. Immunol.* 143, 3781– 3786 (1989). Expression of the recently identified MHC class II transactivator, CIITA, closely parallels that of class II MHC gene expression. V. Steimle et al., *Cell* 75, 135–46 (1993). It has also been shown that CIITA is induced by gamma interferon, and that transfection of CIITA alone into cells is sufficient to activate class II MHC, Ii, and DM genes. See, e.g., C. K. Chin et al., *Immunity* 1, 679 (1994); C. H. Chang et al., *J. Exper. Med.* 180, 1367–1374 (1994); V. Steimle et al., *Science* 265, 106–08 (1994). CIITA transcript is expressed constitutively in class II MHC-positive cells; however, it can be induced in certain cell types such as fibroblasts, macrophages, and glioblastoma cells upon treatment with interferon-γ. See Chang et al., supra; Steimle et al., supra. The kinetic of CIITA induction by interferon-γ precedes the induction of class II MHC transcripts and introduction of CIITA alone into a number of cell types is sufficient to activate class II MHC genes. However, the mode of action of CIITA is not well understood.

The N-terminal of CIITA contains an acidic domain (amino acids 30–160), followed by domains rich in proline (amino acids 163–195), serine (amino acids 209–257), and threonine (amino acids 260–322). Steimle et al., 1993, supra. An acidic domain has been found in many transcription factors and has been shown to interact with basal transcriptional machinery in vitro and in vivo. See, e.g., Schmitz et al., *J. Biol. Chem.* 270, 7219–7226 (1995); Tong et al., *Proc. Natl. Acad. Sci. USA* 92, 3259–3263 (1995). However, it is likely that the acidic domain alone is not sufficient to activate the class II MHC promoter in CIITA, and that the acidic domains of other transcription factors behave differently from the CIITA acidic domain. H. Zhou et al., *Immunity* 2, 545–553 (1995). Analysis of the primary amino acid sequence of CIITA does not show any homology to known conserved DNA-binding motif of transcription factors, and in vitro translated CIITA apparently does not interact with DNA (Steimle et al., 1993, supra).

Proline-, serine-, and threonine-rich domains have been found in many transcriptional factors and may have a role in protein-protein interaction. H. Zhou et al., *Mol. Cell. Biol.* 14, 7013–7024 (1994); T. K. Kim and R. G. Roeder, *Proc. Natl. Acad. Sci. USA* 91, 4170–4174 (1994). However, the role of these and other distinctive domains in CIITA has heretofore been unknown.

SUMMARY OF THE INVENTION

The present invention is based upon an extensive domain analysis to delineate functional domains of CIITA. In addition to the acidic-, proline, serine-, and threonine-rich domains, it has now been found that a GTP-binding domain consisting of phosphate-, $Mg^{2+}$-, and guanine-binding domains to be crucial for CIITA function, strongly suggesting that GTP-binding may be required for CIITA's function. Furthermore, a highly charged region at the C-terminus is also important for function. Collectively, these results suggests that CIITA consists of multi-functional domains including novel domains that have not been previously associated with transcriptional activators or co-activators.

During the course of this analysis, several deletion mutants of the native CIITA protein were created, each containing at least one amino acid deletion in either the proline, serine-, and threonine-rich domain, the GTP-binding domain or the highly charged C-terminus domain.

Accordingly, a first aspect of the invention is a set of isolated and purified mutant CIITA proteins, not naturally occurring, selected from the group consisting of (a) CIITA proteins containing at least one amino acid deletion in the proline/serine/threonine-rich domain; (b) CIITA proteins containing at least one amino acid deletion in a GTP-binding motif domain; and (c) CIITA proteins containing at least one amino acid deletion in the C-terminal domain.

A second aspect of the invention is isolated DNA encoding a mutant class II transactivator (CIITA) protein, selected from the group consisting of: (a) isolated DNA consisting essentially of DNA which encodes a mutant CIITA; (b) isolated DNA of (a) above under conditions represented by a wash stringency of 0.3M NaCl, 0.03M sodium citrate, and 0.1% SDS at 60° C., and which encodes a mutant CIITA; and (c) isolated DNA differing from the isolated DNAs of (a) and (b) above in nucleotide sequence due to the degeneracy of the genetic code, and which encodes a mutant CIITA protein encoded by isolated DNA of (a) or (b) above. Recombinant DNA comprising vector DNA and a DNA as described above, along with host cells containing such recombinant DNA and capable of expressing the same, are also disclosed.

A further aspect of the present invention are antibodies that specifically bind to the CIITAs of the present invention.

The foregoing and other objects and aspects of the present invention are explained in detail in the drawings herein and the specification set forth below.

BRIEF DESCRIPTION OF THE DRAWINGS

In FIG. 2A, the amino acid residues of CIITA from 421 to 561 were aligned with the consensus sequence of GTPase and Ras. The bold letters are sequences within CIITA that are found in the GTPase consensus motifs. The number in the parentheses indicates the spacing between the motifs. FIG. 2B illustrates the mutation of conserved guanine nucleotide-binding domains in the CIITA protein. Mutations were made in the phosphate-binding motifs, CIITA-GTP1(DGK) and CIITA-GTP1(K→E). CIITA-GTP2(DDAYG) contains a deletion in the $Mg^{2+}$-binding motif, DAYG. CIITA-GTP3(DSKAD) contains a deletion in the guanine-binding domain. Bold X indicates the deleted amino acid residue(s). Bold letters represent mutated residues.

DETAILED DESCRIPTION OF THE INVENTION

Amino acid sequences disclosed herein are presented in the amino to carboxy direction, from left to right. The amino and carboxy groups are not presented in the sequence. Nucleotide sequences are presented herein by single strand only, in the 5' to 3' direction, from left to right. Nucleotides and amino acids are represented herein in the manner recommended by the IUPAC-IUB Biochemical Nomenclature Commission, or (for amino acids) by three letter code, in accordance with 37 CFR 1.822 and established usage. See, e.g., PatentIn User Manual, 99–102 (Nov. 1990)(U.S. Patent and Trademark Office).

A. DNA Sequences

DNAs of the present invention include those coding for proteins homologous to, and having essentially the same biological properties as, the proteins disclosed herein, and particularly the DNA disclosed herein as CIITA(Δ132–301), CIITA(Δ132–212), CIITA(Δ209–301), CIITA-GTP1(ΔGK), CIITA-GTP1(K→E), CIITA-GTP2(ΔDAYG), CIITA-GTP-3(ΔSKAD), CIITA(1–931), CIITA(1–949), CIITA(1–1017), CIITA(1–1059), and CIITA(1–1089). This definition is intended to encompass natural allelic variations therein. Isolated DNA or cloned genes of the present invention can be of any species of origin, including mouse, rat, rabbit, cat, porcine, and human, but are preferably of mammalian origin. DNAs which hybridize to DNA disclosed herein as CIITA(Δ132–301), CIITA(Δ132–212), CIITA(Δ209–301), CIITA-GTP1(ΔGK), CIITA-GTP1(K→E), CIITA-GTP2 (ΔDAYG), CIITA-GTP-3(ΔSKAD), CIITA(1–931), CIITA (1–949), CIITA(1–1017), CIITA(1–1059), and CIITA (1–1089) (or fragments or derivatives thereof which serve as hybridization probes as discussed below) and which code on expression for a protein of the present invention are also an aspect of this invention. Conditions which will permit other DNAs which code on expression for a protein of the present invention to hybridize to the DNA disclosed herein can be determined in accordance with known techniques. For example, hybridization of such sequences may be carried out under conditions of reduced stringency, medium stringency or even stringent conditions (e.g., conditions represented by a wash stringency of 35–40% Formamide with 5× Denhardt's solution, 0.5% SDS and 1× SSPE at 37° C.; conditions represented by a wash stringency of 40–45% Formamide with 5× Denhardt's solution, 0.5% SDS, and 1× SSPE at 42° C.; and conditions represented by a wash stringency of 50% formamide with 5× Denhardt's solution, 0.5% SDS and 1× SSPE at 42° C., respectively) to the DNA disclosed herein in a standard hybridization assay. See, e.g., J. Sambrook et al., Molecular Cloning, A Laboratory Manual (2d Ed. 1989)(Cold Spring Harbor Laboratory)). In general, sequences which code for proteins of the present invention and which hybridize to the DNA of CIITA(Δ132–301), CIITA(Δ132–212), CIITA(Δ209–301), CIITA-GTP1(ΔGK), CIITA-GTP1(K→E), CIITA-GTP2(ΔDAYG), CIITA-GTP-3(ΔSKAD), CIITA(1–931), CIITA(1–949), CIITA(1–1017), CIITA(1–1059), and CIITA(1–1089) disclosed herein will be at least 75% homologous, 85% homologous, and even 95% homologous or more with those sequences. Further, DNAs which code for proteins of the present invention, or DNAs which hybridize to those sequences disclosed herein, but which differ in codon sequence from those sequences due to the degeneracy of the genetic code, are also an aspect of this invention. The degeneracy of the genetic code, which allows different nucleic acid sequences to code for the same protein or peptide, is well known in the literature. See, e.g., U.S. Pat. No. 4,757,006 to Toole et al. at Col. 2, Table 1 (applicant specifically intends that the disclosures of all U.S. Patent references disclosed herein be incorporated herein by reference).

B. Genetic Engineering Techniques

The production of cloned genes, recombinant DNA, vectors, transformed host cells, proteins and protein fragments by genetic engineering is well known. See, e.g., U.S. Pat. No. 4,761,371 to Bell et al. at Col. 6 line 3 to Col. 9 line 65; U.S. Pat. No. 4,877,729 to Clark et al. at Col. 4 line 38 to Col. 7 line 6; U.S. Pat. No. 4,912,038 to Schilling at Col. 3 line 26 to Col. 14 line 12; and U.S. Pat. No. 4,879,224 to Wallner at Col. 6 line 8 to Col. 8 line 59.

A vector is a replicable DNA construct. Vectors are used herein either to amplify DNA encoding mutant CIITAs as given herein and/or to express DNA which encodes CIITAs as given herein. An expression vector is a replicable DNA construct in which a DNA sequence encoding a mutant CIITA is operably linked to suitable control sequences capable of effecting the expression of the receptor in a suitable host. The need for such control sequences will vary depending upon the host selected and the transformation method chosen. Generally, control sequences include a transcriptional promoter, an optional operator sequence to control transcription, a sequence encoding suitable mRNA ribosomal binding sites, and sequences which control the termination of transcription and translation.

Amplification vectors do not require expression control domains. All that is needed is the ability to replicate in a host, usually conferred by an origin of replication, and a selection gene to facilitate recognition of transformants.

Vectors comprise plasmids, viruses (e.g., adenovirus, cytomegalovirus), phage, and integratable DNA fragments (i.e., fragments integratable into the host genome by recombination). The vector replicates and functions independently of the host genome, or may, in some instances, integrate into the genome itself. Expression vectors should contain a promoter and RNA binding sites which are operably linked to the gene to be expressed and are operable in the host organism.

DNA regions are operably linked or operably associated when they are functionally related to each other. For example, a promoter is operably linked to a coding sequence if it controls the transcription of the sequence; or a ribosome binding site is operably linked to a coding sequence if it is positioned so as to permit translation.

Transformed host cells are cells which have been transformed or transfected with vectors containing a DNA sequence as disclosed herein constructed using recombinant DNA techniques. Transformed host cells ordinarily express the receptor, but host cells transformed for purposes of cloning or amplifying the receptor DNA do not need to express the receptor.

Suitable host cells include prokaryote, yeast or higher eukaryotic cells such as mammalian cells and insect cells. Cells derived from multicellular organisms are a particularly suitable host for recombinant mutant CIITA synthesis, and mammalian cells are particularly preferred. Propagation of such cells in cell culture has become a routine procedure (Tissue Culture, Academic Press, Kruse and Patterson, editors (1973)). Examples of useful host cell lines are VERO and HeLa cells, Chinese hamster ovary (CHO) cell lines, and WI138, BHK, COS-7, CV, and MDCK cell lines. Expression vectors for such cells ordinarily include (if necessary) an origin of replication, a promoter located upstream from the DNA encoding the mutant CIITA to be expressed and operatively associated therewith, along with a ribosome binding site, an RNA splice site (if intron-containing genomic DNA is used), a polyadenylation site, and a transcriptional termination sequence.

The transcriptional and translational control sequences in expression vectors to be used in transforming vertebrate cells are often provided by viral sources. For example, commonly used promoters are derived from polyoma, Adenovirus 2, and Simian Virus 40 (SV40). See, e.g., U.S. Pat. No. 4,599,308.

An origin of replication may be provided either by construction of the vector to include an exogenous origin, such as may be derived from SV 40 or other viral (e.g. Polyoma, Adenovirus, VSV, or BPV) source, or may be provided by the host cell chromosomal replication mechanism. If the vector is integrated into the host cell chromosome, the latter is often sufficient. Rather than using vectors which contain viral origins of replication, one can transform mammalian cells by the method of cotransformation with a selectable marker and the receptor DNA. Examples of suitable selectable markers are dihydrofolate reductase (DHFR) or thymidine kinase. This method is further described in U.S. Pat. No. 4,399,216.

Other methods suitable for adaptation to the synthesis of the mutant CIITA in recombinant vertebrate cell culture include those described in M-J. Gething et al., *Nature* 293, 620 (1981); N. Mantei et al., *Nature* 281, 40 (1979); A. Levinson et al., EPO Application Nos. 117,060A and 117, 058A.

Host cells such as insect cells (e.g., cultured *Spodoptera frugiperda* cells) and expression vectors such as the baculovirus expression vector (e.g., vectors derived from *Autographa californica* MNPV, *Trichoplusia ni* MNPV, *Rachiplusia ou* MNPV, or *Galleria ou* MNPV) may be employed in carrying out the present invention, as described in U.S. Pat. Nos. 4,745,051 and 4,879,236 to Smith et al. In general, a baculovirus expression vector comprises a baculovirus genome containing the gene to be expressed inserted into the polyhedrin gene at a position ranging from the polyhedrin transcriptional start signal to the ATG start site and under the transcriptional control of a baculovirus polyhedrin promoter.

Prokaryote host cells include gram negative or gram positive organisms, for example, *Escherichia coli* (*E. coli*) or Bacilli. Higher eukaryotic cells include established cell lines of mammalian origin as described below. Exemplary host cells are *E. coli* W3110 (ATCC 27,325), *E. coli* B, *E. coli* X1776 (ATCC 31,537), *E. coli* 294 (ATCC 31,446). A broad variety of suitable prokaryotic and microbial vectors are available. *E. coli* is typically transformed using pBR322. Promoters most commonly used in recombinant microbial expression vectors include the beta-lactamase (penicillinase) and lactose promoter systems (Chang et al., Nature 275, 615 (1978); and Goeddel et al., *Nature* 281, 544 (1979)), a tryptophan (trp) promoter system (Goeddel et al., *Nucleic Acids Res.* 8, 4057 (1980) and EPO App. Publ. No. 36,776) and the tac promoter (H. De Boer et al., *Proc. Natl. Acad. Sci.* USA 80, 21 (1983)). The promoter and Shine-Dalgarno sequence (for prokaryotic host expression) are operably linked to the DNA encoding the mutant CIITA i.e., they are positioned so as to promote transcription of mutant CIITA messenger RNA from the DNA.

Eukaryotic microbes such as yeast cultures may also be transformed with vectors carrying the isolated DNA's disclosed herein. See, e.g. U.S. Pat. No. 4,745,057. *Saccharomyces cerevisiae* is the most commonly used among lower eukaryotic host microorganisms, although a number of other strains are commonly available. Yeast vectors may contain an origin of replication from the 2 micron yeast plasmid or an autonomously replicating sequence (ARS), a promoter, DNA encoding the receptor as given herein, sequences for polyadenylation and transcription termination, and a selection gene. An exemplary plasmid is YRp7, (Stinchcomb et al., *Nature* 282, 39 (1979); Kingsman et al., *Gene* 7, 141 (1979); Tschemper et al., *Gene* 10, 157 (1980)). Suitable promoting sequences in yeast vectors include the promoters for metallothionein, 3-phosphoglycerate kinase (Hitzeman et al., *J. Biol. Chem.* 255, 2073 (1980) or other glycolytic enzymes (Hess et al., *J. Adv. Enzyme Reg.* 7, 149 (1968); and Holland et al., *Biochemistry* 17, 4900 (1978)). Suitable vectors and promoters for use in yeast expression are further described in R. Hitzeman et al., EPO Publn. No. 73,657.

DNAs of the present invention are useful in gene therapy. For such purposes, retroviral vectors as described in U.S. Pat. No. 4,650,764 to Temin and Watanabe or U.S. Pat. No. 4,861,719 to Miller may be employed. DNAs of the present invention, or fragments thereof, may also be used in gene therapy carried out by homologous recombination or site-directed mutagenesis. See generally K. Thomas and M. Capecchi, *Cell* 51, 503–512 (1987); W. Bertling, *Bioscience Reports* 7, 107–112 (1987); O. Smithies et al., *Nature* 317, 230–234 (1985).

The following Examples are provided to more fully illustrate the present invention, and are not to be construed as limiting thereof.

EXAMPLE 1

Plasmid Construction

The mammalian expression vector, pcDNA3.FLAG.CIITA8 (FLAG.CIITA8), contains the FLAG epitope (DYKDDDDK) in front of the first methionine of CIITA8. The FLAG.CIITA hybrid gene was driven by a CMV promoter in the pcDNA3 vector (In Vitrogen, San Diego, Calif.). The pcDNA3 expression vector contains a SV40 promoter linked to a neomycin gene, which confers resistance to the antibiotic G418. Construction of FLAG.CIITA8 was as follows:

Two oligonucleotides were annealed and filled in with the Klenow enzyme. The upper strand oligonucleotide was as follows:

```
5'- CCGGAATTCATGGACTACAAAGACGATGA        (SEQ ID NO:1)
    CGATAAAATGCGTTGCCTGGCTCCACGCCC
    TGCTGGGTCCTACCTGTCAGAGCCCCAAG -3'
``` which contains an EcoRI site, a methionine, the FLAG epitope (DYKDDDK) and the first 17 amino acid residues of CIITA8. The lower strand was as follows:

```
5'- CCGGAATTCATGGACTACAAAGACGATGA        (SEQ ID NO:2)
    CGATAAAATGCGTTGCCTGGCTCCACGCCC
    TGCTGGGTCCTACCTGTCAGAGCCCCAAG -3'
``` which consists of amino acid residues 11 to 27 of CIITA8, followed consecutively by BstXI, BstXI, and EcoR1 sites. The double-stranded DNA was digested with EcoRI, and cloned into the EcoRI site of pAR(ΔRI) 59/60 (M. A. Blanar and W. J. Rutter, *Science* 256, 1014–1018 (1992)), resulting in a chimeric plasmid named pAR(ΔRI) 59/60.FLAG. CIITA8 cDNA was released from pREP4.CIITA8 (Riley et al., *Immunity* 2, 533–543 (1995)) with BstXI, and cloned into the BstXI site of pAR(ΔRI) 59/60.FLAG vector. The FLAG.CIITA8 was then released by EcoRI and cloned into the EcoRI-digested pcDNA3. The direction was confirmed first by BamHI digestion, and then by direct sequencing. This construct was named FLAG.CIITA8.

All mutant constructs were generated by the method described by Deng et al., *Anal. Biochem.* 200, 81–88 (1992), with a modification in which T4 DNA polymerase was replaced with T7 DNA polymerase. All mutants were generated from the parental plasmid, FLAG.CIITA8, with a selection primer:

```
5'-AAATGCTTCAATgcTAGcgAAAAAGGAAG-3'   (SEQ ID NO:3)
``` which mutated a SspI to NheI restriction site, and a mutagenic primer. All mutants were initially identified by the presence of an NheI site, and later confirmed by sequencing.

EXAMPLE 2

Construction of Proline/Serine/Threonine Deletion Mutants

The deletion mutant CIITA(Δ132–301) was constructed by creating ClaI restriction sites at nucleotides 511 (amino acids 132–133), and 1013 (amino acids 300–301) of CIITA8 using the following two mutagenic primers:

```
5'-533-GCCCAACTTCTGCTGGCATaTCgATA       (SEQ ID NO:4)
CTCTCACCGATCAC-493-3'
``` and

```
5'-1036-GAGGTCAGGGCAGGTTCAtcgATG        (SEQ ID NO:5)
CTGGGCAGGTCAGTG-997-3'
```

The mutagenized construct was digested with ClaI to release the proline/serine/threonine-containing fragment. The remaining sequence in the plasmid was then religated. The deletion mutant CIITA(Δ132–212) was constructed in the same way as mentioned above with mutagenic primers:

```
5'-533-GCCCAACTTCTGCTGGCATaTCgATA       (SEQ ID NO:6)
CTCTCACCGATCAC-493-3'
``` and

```
5'-766-CAACGAGGAACTGGAGAAAtcgATGG       (SEQ ID NO:7)
GAATCTGGTCGGTTTTC-724-3'
``` and it contained a clean deletion of the proline-rich domain.

The deletion mutant CIITA(Δ209–301) has deleted threonine-rich domains from amino acid residues of 209 to 301. This mutant construct was mutagenized with the following primers:

```
5'-766-CAACGAGGAACTGGAGAAAtcgATG        (SEQ ID NO:8)
GGAATCTGGTCGGTTTTC-724-3'
``` and

```
5'-1036-GAGGTCAGGGCAGGTTCAtcgATG        (SEQ ID NO:9)
CTGGGCAGGTCAGTG-9979-3'
```

EXAMPLE 3

Construction of Nucleotide-Binding Motifs Mutants

CIITA-GTP1(ΔGK), and CIITA-GTP1(K→E) were mutated in the phosphate-binding motif CIITA-GTP1(ΔGK)

has a deletion of two amino acid residues and GK (amino acids 420–421) by a "loop out" mutagenic primer:

5'-1395-CTCTTGCCCTGACCAGCCACAGCAAT (SEQ ID NO:10)
CACTCGTG-1353-3'

CIITA-GTP1(K→E) has a point mutation at residue 427 from lysine to glutamic acid. The mutagenic primer used to generate this mutant was:

5'-1408-CCCAGCCCAATAGCTCTCGCCCTGACCA (SEQ ID NO:11)
GCTTTGCC-1073-3'

CIITA-GTP2(ΔDAYG) and CIITA-GTP3(ΔSKAD) have deletions respectively in the $Mg^{2+}$- and guanine-binding motifs. CIITA-GTP2(ΔDAYG) was created by a "loop out" primer:

5'- 1522- (SEQ ID NO:12)
GAGCAGATCCTGCAGCCCCGGACGGTTC
AAG-1480-3'

The mutagenic primer used to construct GTP3(ΔSKAD) was:

5'-1813-CAGCTCAAATAGGGCCAGGCTCTGGAC (SEQ ID NO:13)
CAG-1777-3'

EXAMPLE 4

Construction of C-Terminal Deletion Mutants

All C-terminal deletion mutants were constructed by mutating a specific amino acid residue to a stop codon. The mutagenic primers and position of stop codon were shown as follows:

| Mutants | Mutagenic Primers | Stop Codon Position |
|---|---|---|
| CIITA(1–931) | 5'-2926-GTCTGCACAAG CTTTCaCAAATCT TCCACATCC-2879-3' (SEQ ID NO: 14) | G 932 |
| CIITA(1–949) | 5'-2979-CGAACAGCAGG GAGCTaCCCAGCTGTGT CTTCCG-2946-3' (SEQ ID NO: 15) | E 950 |
| CIITA(1–1017) | 5'-3395-CAGCGAGCTGCT aGGCCCCGGCAG-3371-3' (SEQ ID NO: 16) | E1018 |
| CIITA(1–1059) | 5'-3281-CAAGCTCTCGGCTC aCACGTCGCAGATG-3281-3' (SEQ ID NO: 17) | G 1060 |
| CIITA(1–1089) | 5'-3179-GATTGAGGGTTa CAAGGACTTCAGC-3154-3' (SEQ ID NO: 18) | Q 1090 |

EXAMPLE 5

Cell Cultures

In order to understand how CIITA functions, the consequences on DRA promoter activation were assessed by introducing the above mutants into a CIITA-negative, IFN-γ defective mutant cell, G3A (Chin et al., 1994, supra).

2fTGH, and G3A cells were grown in Dulbecco's Modified Eagle Media (DMEM-H) containing heat-inactivated 10% fetal calf serum (FCS) (Gibco BRL, Grand Island, N.Y.) as previously described (C. Mao et al., *Proc. Natl. Acad. Sci.* USA 90, 2880–2884 (1993); K. C. Chin et al., *Immunity* 1, 687–97 (1994)). 2fTGH is derived from a fibrosarcoma cell line (HT 1080) that does not express class I MHC antigen constitutively, but expresses a high level of class II MHC antigens after IFN-γ induction. G3A is a class I MHC-negative cell line generated by mutagenesis and can be rescued to re-express class II MHC molecules by CIITA gene. The Raji and Namalwa cell lines are from human Epstein-Barr virus-positive Burkitt lymphoma lines and constitutively express a high level of class II MHC antigens. RJ2.2.5 is a class II MHC-negative mutant B cell derived from Raji cells. R. S. Accolla, *J. Exper. Med.* 157, 1053–1058 (1983). Raji, Namalwa, and RJ2.2.5 cells were maintained in RPMI 1640 supplemented with 10% fetal calf serum and 2 mM L-glutamine (Gibco BRL, Grand Island, N.Y.). COS-7 is a T-antigen transformed monkey kidney cell line, and was maintained in DMEM-H media containing 10% fetal calf serum and 1× nonessential amino acids (Gibco BRL, Grand Island, N.Y.).

EXAMPLE 6

Transient Transfection

Transactivation is measured by the activation of the DRA promoter in a CIITA-deficient, IFN-γ nonresponsive mutant line, G3A.

2fTGH, and G3A cells were transfected by the calcium phosphate co-precipitation method as described previously (Chin et al., supra). Ten μg of pDRACAT300 (P. A. Sherman et al., *Molec. Cell. Biol.* 9, 50–56 (1989)) and 10 μg of expression plasmids were used in each of the transfection. Cells were harvested for CAT assays after 48 hours of transfection, and the percentage of acetylation was quantitated by phosphorimaging (Molecular Dynamics, Sunnyvale, Calif.).

COS-7 cells were transfected by lipofectamine reagent (Gibco BRL, Grand Island, N.Y.). Briefly, $5 \times 10^5$ of COS-7 cells were plated in 60 mm dish (Costar, Cambridge, Mass.) and transfected 24 hours after plating. Two μg of wild-type CIITA (FLAG.CITTA8) or control vector DNA (pcDNA3) were used in the transfection. The cells were incubated with plasmid DNA and lipofectamine reagent (Gibco BRL, Grand Island, N.Y.) for 8 hours, and the media were removed and replaced with fresh DMEM-H media containing 10% fetal calf serum and 1× nonessential amino acid. The cells were harvested 24 hours later and whole cell extracts were prepared as described in Example 8 below.

RJ2.2.5 cells were transfected by electroporation as described by P. V. Basta et al., *Proc. Natl. Acad. Sci.* USA 85, 8618–8622 (1988) with some modification. Briefly, $3.5 \times 10^6$ cells in 300 ul of complete medium were pulsed at 200V at a capacitance of 960 μF. Twenty μg of FLAG-CIITA8 was used in each transfection.

EXAMPLE 7

Stable Transfectants Expressing Cell-Surface MHC Class II Antigen with FLAG.CIITA8 Expression Vector Ten μg of FLAG.CIITA8 plasmid were transfected into G3A cell as described above. The G3A cell line itself is neomycin resistant; accordingly, it cannot be selected by a standard drug selection. The stable transfectants expressing cell-surface MHC class II antigens were selected by the immuno-magnetic selection, according to the instruction of manufacturer. Briefly, the transfected cells (approximately $5\times10^6$ cells) were detached from two culture plates with 1× trypsin EDTA 72 hours after the start of transfection, washed 3 times with 1× HBSS containing 2.5% of FCS (HBSSF). The cells were resuspended in HBSSF containing L243 (1:50), a HLA class II MHC-specific monoclonal antibody, and incubated for 30 minutes by rotating on the nutator at 4° C. After 30 minutes of incubation, the cells were washed with HBSSF three times. Magnetic beads ($2\times10^7$) conjugated to the goat-anti-mouse Ig (Dynal, Norway) were added to the cells and incubated for another 30 minutes in HBSSF. After a 30 minute incubation, cells with attached bead and free beads were pulled down with a cobalt-samarium magnet rack (Promega, Madison, Wis.). The cells were washed two times and resuspended in 10 ml of DMEM-H media containing 15% of FCS and replated in 10 cm of culture plate. The cells underwent immunoselection three times for the next four weeks. The cells expressing MHC class II antigens were confirmed by FAC analysis as described (Chin et al., supra).

EXAMPLE 8

Western Blots

Raji, Namalwa, and RJ2.2.5 nuclear extracts were prepared according to Dignam et al., *Nucleic Acids Res.* 11(5), 1475–89 (1983). Whole cell extracts were prepared by lysing the cells in NP-40% lysis buffer (20 mM NaCl, 50 mM Tris.HCl, pH 8, 10% glycerol, 1 mM EDTA, 0.5% NP-40, 1 mM PMSF, 10 mg/ml of aprotonin, and 10 mg/ml of leupeptin), and was mixed in a nutator for 30 minutes at 4° C., and then centrifuged at 14,000 rpm in a microcentrifuge at 4°C. for 15 minutes. The supernatant was transferred to a fresh tube and stored in aliquot at −70° C. Samples were resuspended in Laemmli sample buffer, and boiled for 3 minutes. The samples were resolved in 8% SDS-PAGE (29 acrylamide; 1 bisacrylamide), and analyzed by immunoblotting with α-FLAG (10 mg/ml) (IBI Kodak), or α-CIITA (1.5 mg/ml) antibodies using standard techniques. Immunoblots were detected by enhanced chemical luminescence (ECL), according to the manufacturer (Amersham, Arlington Heights, Ill.).

EXAMPLE 9

Proline/Serine/Threonine Rich Region and Transactivation Activity of CIITA

Figure 1:
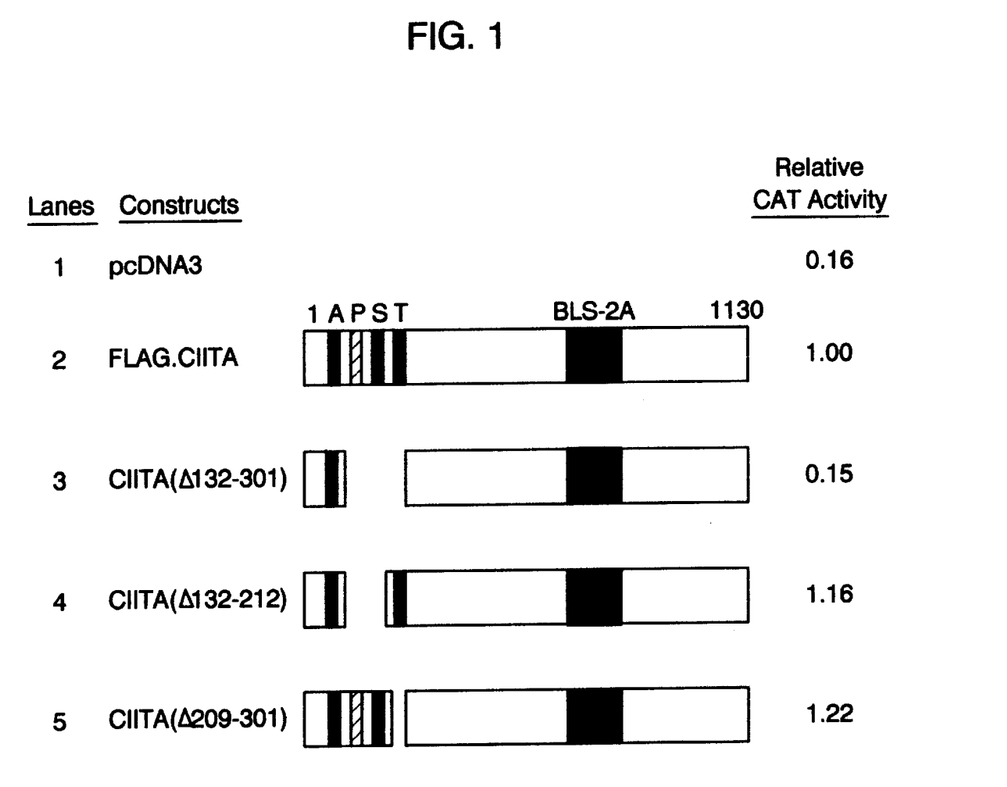
FIG. 1 illustrates the requirement for proline/serine-rich or threonine-rich domain in addition to the acidic domain for CIITA activity. G3A cells were co-transfected with the pDRACAT300 and either pcDNA3 (lane 1), FLAG.CIITA (lane 2) or mutant constructs (lanes 3 to 5). The cells were harvested 48 hours after transfection. CAT activity was analyzed and quantitated by phosphorimaging. The relative level of expression was calculated by using the wild-type control as a value of 1.
Figure 3:
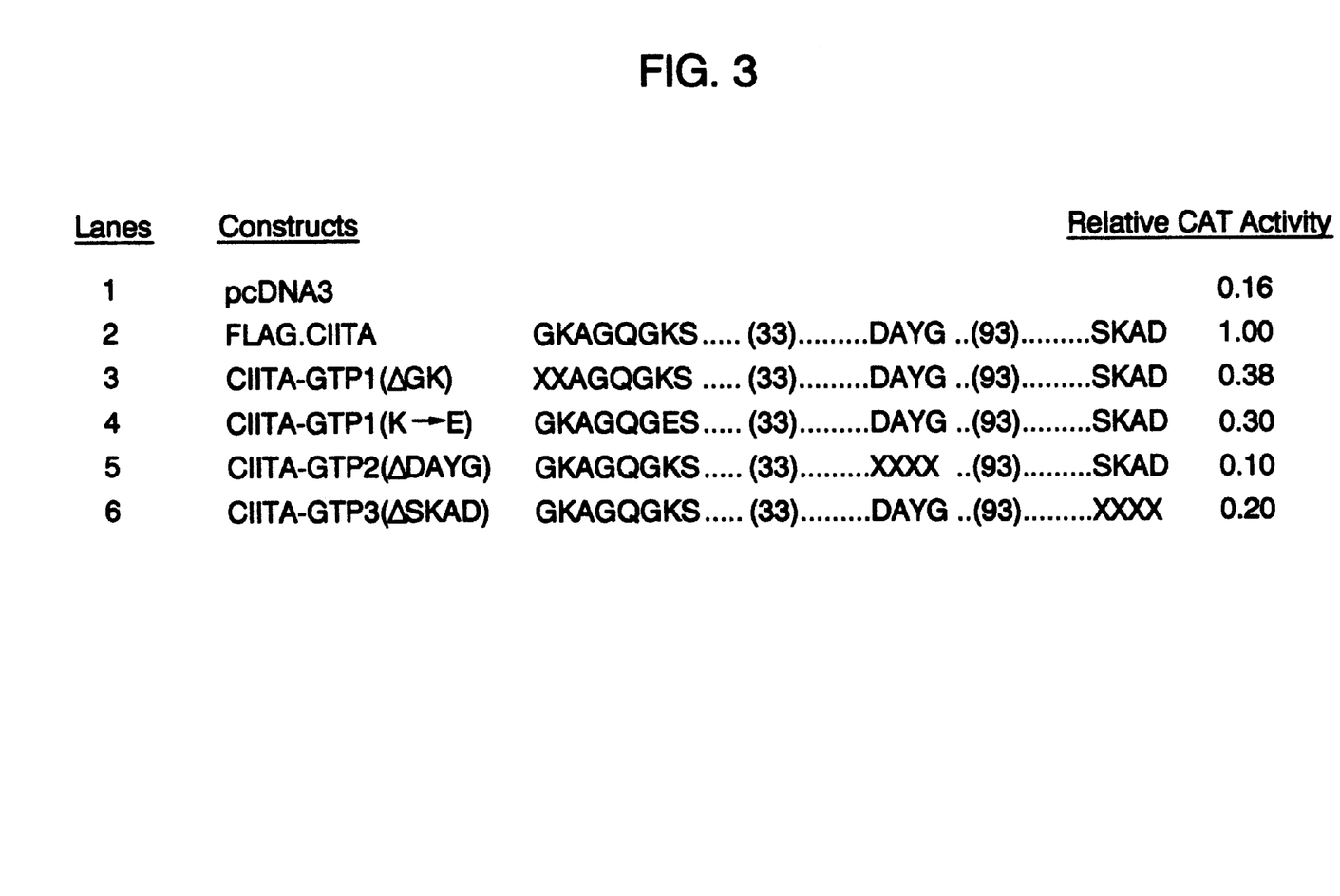
FIG. 3 illustrates that guanine nucleotide-binding motifs are essential for CIITA activity. G3A cells were co-transfected with the pDRCAT300 and pcDNA3 (lane 1), FLAG.CIITA (lane 2), or mutant CIITA (lanes 3 to 6). Cells were harvested 48 hours later and CAT activity was determined as described below in the Examples section.

A mutant CIITA, named CIITA(Δ132–301) and shown in FIG. 1, retains the acidic domain but deletes the proline-, serine-, and threonine-rich domains (amino acids 132 to 301), and was used to analyze this region. This mutant did not exhibit any activation activity when transfected with pDRA300CAT (FIG. 1, compare lanes 3 with 2) which suggests that the acidic domain alone was not sufficient to activate the class II MHC promoter and intact proline-, serine-, and threonine-rich regions are also necessary. To better define the function of proline-, serine-, and threonine-rich domains of CIITA, two mutants, CIITA(Δ132–212) and CIITA(Δ209–301), were made. CIITA (Δ132–212) has a clean deletion of the proline-rich domains (amino acids 132 to 212), and this deletion did not affect the activation of DRA promoter by CIITA (FIG. 1, compare lanes 4 to 2). Deletion of the serine/threonine-rich domain in mutant (CIITA (Δ209–301) also did not affect transactivation function (FIG. 3A, compare lanes 5 to 2). This suggests that the two subdomains may serve overlapping functions.

To ascertain that the low activity of these mutants was not due to the low expression of mutant protein, cells were transfected with the wild-type FLAG.CIITA8 or the mutants CIITA(Δ132–301), (CIITA(Δ132–212), CIITA(Δ209–301). Whole cell extracts were made 24 hours after transfection, according to procedures described in Example 8. An equivalent amount of total lysates from each sample was fractionated on 8% SDS-PAGE gel. The whole cell extracts were separated by SDS-PAGE and blotted with the α-CIITA antibody. The immunoblot analysis showed that the mutants produced comparable levels of protein as the wild-type construct, FLAG.CIITA8 (data not shown). No specific band was detected in cells transfected with the control vector (data not shown). These results were also confirmed with the antibody against the FLAG-epitope.

EXAMPLE 10

CIITA Function Requires A GTP-Binding Motif

Figure 2A:
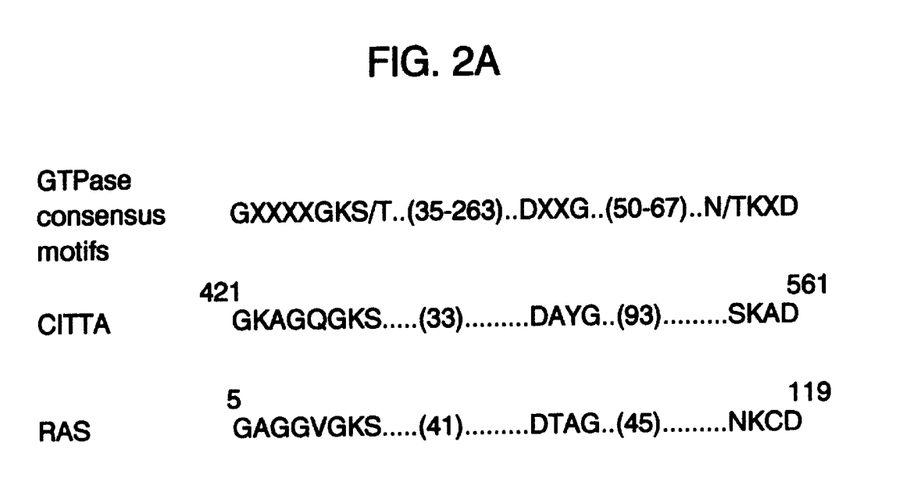
FIGS. 2A and 2B illustrate the analysis of guanine nucleotide-binding motifs within CIITA.

Analysis of the primary amino acids of CIITA shows that a region of CIITA from residues 421 to 561 has a significant homology to a wide variety of GTP-binding proteins in the Ras superfamily including the low-molecular-weight Ras-like GTPase, the translation elongation factor (EF-TU), and the a submits of heterotrimeric G protein. T. E. Dever et al., *Proc. Natl. Acad. Sci.* USA 84, 1814–18 (1987). CIITA exhibits similarities to three consensus motifs found in other GTP-binding domains; the phosphate-binding motif GXXXXGKS, the $Mg^{2+}$-binding motif DXXG, and the guanine-binding motif SKXD (FIG. 2A). These sequence motifs are also referred to as G-1, G-3 and G-4, respectively. The G-1 region of CIITA($GX_4GKS$) has a perfect match to the conserved amino acid sequence of p21$^{ras}$ ($^{10}GX_4GKS^{17}$). The X-ray structure of p21$^{ras}$ (shows this region is a loop in which the main-chain amide hydrogens of several amino acids and the -amino group of Lys$^{16}$ (corresponding to Lys$^{427}$ of CIITA) forms bonds with the a and P-phosphate of GTP or GDP. See, E. F. Pai et al., *EMBO J.* 9, 2351–2359 (1990); M. V. Milburn et al., *Science* 247, 939–945 (1990). The G-3 region, $^{461}DX_2G^{464}$ of CIITA is also conserved and it corresponds to residues 57–60, $^{57}DX_2G^{60}$, of p21$^{ras}$, In p21$^{ras}$, the invariant aspartate (position 461 in CIITA) binds the catalytic $Mg^{2+}$ through an intervening water molecule, while the amide proton of the invariant glycine (position 464 of CIITA) forms a hydrogen bond with γ-phosphate of GTP. The G-4 region of CIITA, $^{558}SKXD^{561}$, is identical to the p21$^{ras}$ G-4 region (residues 116–119, $^{116}NKXD^{119}$) except position 558 of CIITA has serine residue instead of a asparagine or threonine residue and this change did not affect CIITA's function. N$^{116}$, together with lysine$^{117}$ stabilize the guanine nucleotide binding site of p21$^{ras}$ through hydrogen bonds to residues 13 and 14 in the G-1 region. The invariant Asp$^{119}$ forms hydrogen bonds with the guanine ring. Collectively, these homologies suggest the likelihood that CIITA exhibits guanine nucleotide-binding activity.

Figure 2B:
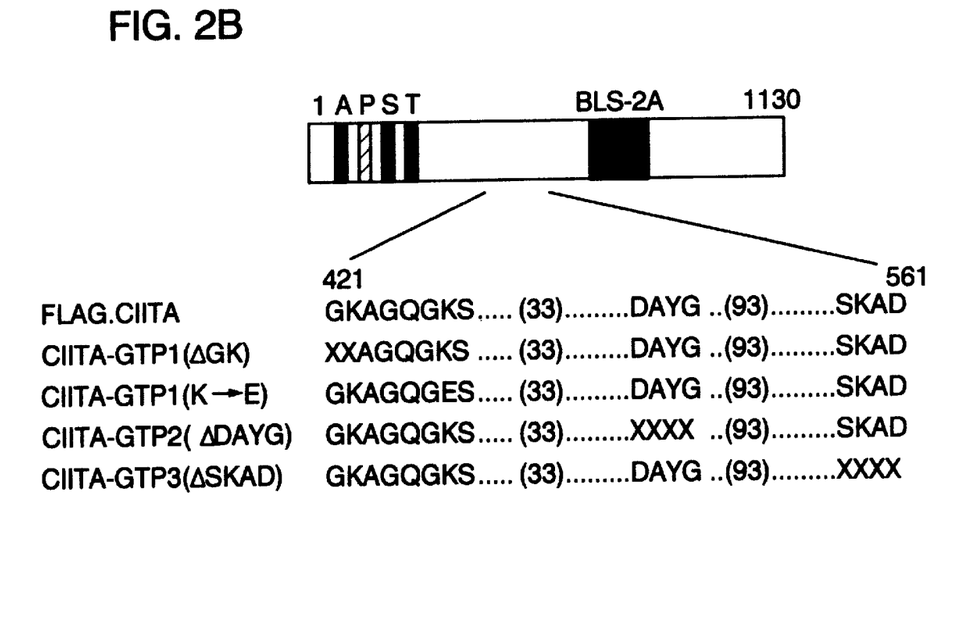

To determine if these motifs are significant, each motif was individually mutated (FIG. 2B) and examined for effects on transactivation activity. The mutants were co-transfected with the pDRA300CAT into G3A cells and CAT activity was determined. As shown in FIG. 3, CIITA-GTP1(ΔGK), which contained a deletion of residues 421 to 422 in the phosphate-binding motif, showed a reduced transactivation activity (22% above the basal activity and 38% of the wild-type controls (FIG. 3, lanes 1 to 3). CIITA-GTP1(K→E) contains a substitution of lysine$^{427}$(K) to glutamin acid (E). X-ray crystallography of Ras and EF-TU shows that this is a crucial residue which forms bonds with the α- and β-phosphates of GTP or GDP. See Pai et al.,; Milburn et al., supra. Therefore, mutation in this residue should have an effect on the function of CIITA if it is involved in nucleotide binding. Indeed, CIITA-GTP1(K→E) exhibits greatly reduced activity (FIG. 3, lane 4). The transactivation capability of CIITA-GTP2(ΔDAYG) and CIITA-GTP3(ΔSKAD) constructs was then examined. These two constructs contain deletion in the Mg$^{2+}$-binding motif and guanine-binding motif, respectively. These two constructs completely failed to activate the DRA promoter (FIG. 3, lanes 5 and 6). It was noted that p21$^{ras}$ deletion of the Mg$^{2+}$-binding site, $^{57}$DX$_2$G$^{60}$, abolishes its transformation activity (S. K. Srivastava et al., *Molec. Cell. Biol.* 9, 1779–1783 (1989)), while the CIITA-GTP2(ΔDAYG) mutant also fails to activate the class II MHC promoter.

A Western blot was performed according to procedures described above, in order to assess the level of protein expression by mutant CIITA genes. An equal amount of total lysates was loaded, separated on SDS-PAGE and transferred onto nitrocellulose. The blot was probed with the α-CIITA antibody. The results of the blot analysis confirmed that all constructs expressed CIITA at a comparable level to the wild-type protein (data not shown). The only exception was the mutant CIITA-GTP2(ΔDAYG), which showed a lower level of protein expression. This is consistent with previous reports which show that GTP-binding proteins are often unstable when this region is mutated, and that this region is crucial for protein stability. See, e.g., R. Foster et al., *Mol. Cell Biol.* 14, 7173–7181 (1994); J. Feuerstein et al., *J. Biol. Chem.* 262, 8455–8458 (1987). These results, in total, strongly suggest that CIITA contains putative GTP-binding motifs.

EXAMPLE 11

Characterization of C-Terminal Region of CIITA

Figure 4:
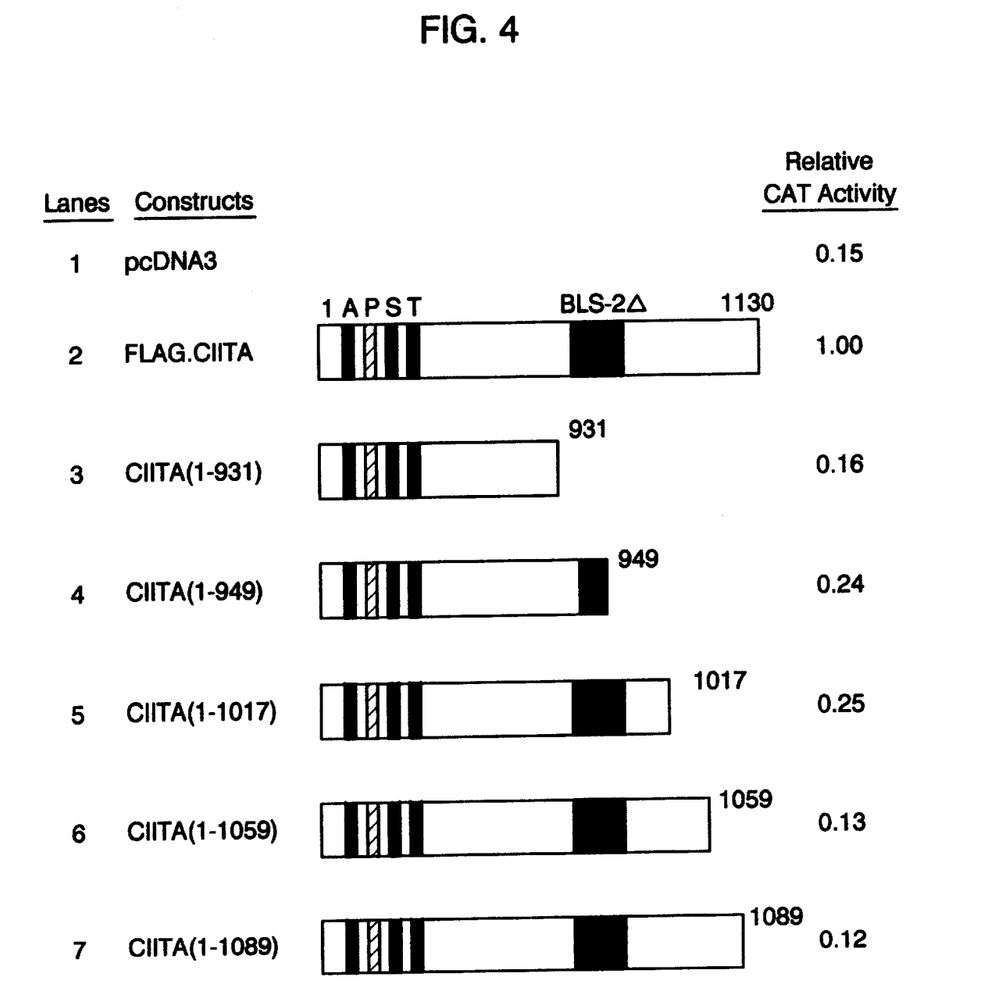
FIG. 4 illustrates the result that CIITA mutants lacking the C-terminal 41 amino acids lack transactivation capability. The control vector pcDNA3 (lane 1), FLAG.CIITA (lane 2) and mutant CIITA constructs (lanes 3 to 7) were co-transfected with pDRCAT300 into G3A cells. CAT activity was determined 48 hours after transfection.

BLS-2 is patient-derived cell line which lacks class II MHC expression at both the protein and RNA levels. Steimle et al. (1993), supra, reported that wild-type CIITA can restore the class II MHC expression on BLS-2 cells. The major mutation in BLS-2 is a defective splice donor, resulting in a deletion of residues 940–963 designated as BLS-2A, and this deletion produces a non-functional CIITA. Here, we show that sequences downstream of the BLS-2A region also play a functional role in class II MHC transactivation. A series of progressive deletion mutants were constructed (FIG. 4). CIITA(1–931) has a deletion from residue 932 to residue 1130. This deletion includes the region missing in BLS-2 cells. As expected, it did not exhibit transacting activity (FIG. 4, lane 3). A second deletion mutant, CIITA (1–949), retained the first 11 amino acid residues deleted in BLS-2, and it also showed little transactivation activity (FIG. 4, lane 4). Mutants with progressive smaller C-terminal deletions CIITA(1–1017), CIITA(1–1059), and CIITA(1-1089) still showed little capacity to transactivate the class II MHC promoter (FIG. 4, lanes 5, 6, and 7). This latter group of mutants does not have any mutations in the region that is missing in BLS-2. The data indicated that the C-terminal 41 amino acids downstream of the BLS-2 deletion as defined by the construct CIITA(1–1089) is also important for CIITA activity.

The size and level of these mutant proteins were examined by Western Blot analysis, as described above. Mutants and wild-type FLAG.CIITA were detected by anti-CIITA antibody. Anti-CIITA antibody does not detect any CIITA protein in cells transferred with the control vector, pcDNA3. The mutants were expressed at a comparable level as wild-type CIITA, with migration patterns that agreed with the predicted apparent molecular weights (data not shown).

EXAMPLE 12

Anti-CIITA(α-CIITA) Antibody Production

Antibodies to native CIITA and epitope-tagged CIITA protein are used to verify that these mutant proteins are expressed as well as the wild-type control. Anti-human CIITA antibody was raised against a peptide, $^{726}$CGEIKD-KELPQYLALTPR$^{742}$ crosslinked to KLH (Keyhold Limpet Hamocyanin) (Pierce, Rockford, Ill.). The antiserum was tested after numerous injections of the rabbit with the antigen.

EXAMPLE 13

Generation and Characterization of CIITA Antibody

To accurately assess the effects of mutagenesis on CIITA, it was verified that mutant proteins were expressed to a similar level as wild-type controls. Several reagents were generated to assess this issue. First, a FLAG epitope-tagged CIITA was produced. FLAG was chosen because antibodies against this epitope have been used widely in supershift, staining and immunoprecipitation (IBI, Kodak). This epitope is small (8 amino acids); thus, the probability that it disrupts the native conformation of CIITA is small.

FLAG epitope-tagged CIITA, named FLAG.CIITA8, was found to function equally well as wild-type CIITA in trans-activating class I MHC promoter, as assessed by both CAT reporter gene analysis and surface class II MHC antigen expression analysis. In the CAT reporter gene analysis, either FLAG-tagged or unmodified CIITA-expression vector was transfected together with DRA300CAT into a CIITA-defective cell line, G3A. pDRA300CAT contains 267 bp of the DRA promoter linked to chloramphenicol acetyltransferase (CAT) reporter gene (Sherman et al., supra. G3A cells were co-transfected with the pDRACAT300 construct and either an empty vector, CIITA expression vector, or FLAG.CIITA. The cells were harvested and analyzed for CAT activity 48 hours after transfection. The results of this experiment illustrated that FLAG.CITTA activates the DRA promoter in G3A cells, and thus showed that FLAG-tagged CIITA functioned properly in the transactivation assay (data not shown).

In the MHC antigen expression analysis, G3A cells were transfected according to the procedures used in the CAT reporter gene analysis. The results were analyzed by flow cytometry. Specifically, 2fTGH cells, G3A, and G3A stably integrated with FLAG.CITTA) were either untreated or treated with 300 U/ml of IFN-γ for 72 hours. The cells were harvested and analyzed for surface HLA-DR antigen expression by a FACScan. The wild-type parent, 2fTGH, was responsive to IFN-γas expected, while the G3A cell line was not (data not shown). Transfection of FLAG-tagged CIITA into G3A cells resulted in high levels of surface class I MHC (data not shown). These results illustrate that FLAG.CIITA induces HLA-DRA expression on the class II MHC-negative G3A mutant cells. Together, the CAT reported gene analysis and the MHC antigen analysis illustrate that the FLAG foreign epitope does not alter CIITA activity.

The expression of recombinant CIITA protein in 2fTGH and COS-7 cells transfected with FLAG.CIITA8 was examined by Western blot analysis. 2fTGH and COS-7 cells were transfected respectively with I 0 mg and 2 mg of either FLAG.CIITA or empty vector pcDNA3. The cells were harvested 24 hours after the transfection and total lysates were prepared and separated on a 8% SDS-PAGE gel. The gel was transferred onto nitrocellulose and the presence of recombinant CIITA was examined with 10 mg/ml of α-FLAG antibody. Recombinant CIITA migrated at an apparent molecular weight of 145 kd in SDS-PAGE, and specifically was recognized by the α-FLAG antibody. A signal was found in extracts prepared from cells transfected with FLAG.CIITA8 but not the control vector, pcDNA3 (data not shown).

The specificity of α-CIITA of this antibody was tested using extracts from 2fTGH and RJ2.2.5 cells transfected with pcDNA3 or FLAG.CIITA8. 2fTGH and RJ2.2.5 cells were transfected with either FLAG.CIITA or control vector pcDNA3. Total lysates were prepared and examined with either α-FLAG antibody, α-CIITA antibody, or pre-immune serum. Whole cell extracts were made 24 hours after transfection, and the lysates were separated on an SDS-PAGE gel. The blots were then incubated with α-FLAG and α-CIITA antibodies and preimmune serum. The patterns for both antibodies are identical indicating that the α-CIITA antibody indeed recognized the appropriate molecule. Both antibodies recognized a band of 145 kd in FLAG.CITTA8 transfected 2fTGH and RJ2.2.5 cells (data not shown). This band was not observed in 2fTGH cells transfected with the empty vector, nor in a blot incubated with preimmune serum. These results indicate that the α-CIITA antibody specifically recognizes recombinant CIITA.

The recognition of endogenous CIITA by the α-CIITA antibody in two B cell lines was a final test of this antibody. One Raji and two Namalwa nuclear extracts were prepared according to Dignam et al. (1983) and separated on the 8% SDS-PAGE. The blot was then probed with either the α-FLAG antibody, α-CIITA antibody, or preimmune serum. A 145 kd band which migrated at the same position as recombinant CIITA was detected by the α-CIITA antibody (data not shown). The same band was not observed when using the α-FLAG antibody or preimmune serum which should not detect the endogenous, unmodified CIITA. This series of experiments confirm the specificity of the α-CIITA antibody. Also, this band was not detected in RJ2.2.5 cells which produces a CIITA that lacks the epitopes recognized by the α-CIITA antibody.

These results illustrate that anti-CIITA antibody specifically recognizes an endogenous CIITA with an apparent molecular weight of 145 kd.

EXAMPLE 14

Transdominant Negative Mutants of CIITA

CIITA represents a highly specific, yet potent, regulator of class II MHC genes. Any interference with its function is likely to significantly affect antigen presentation by class II MHC-mediated pathway and subsequent T cell activation; such interference may be desirable in a number of diseases.

The capacity of multiple mutant forms of CIITA to serve as decoy molecules, hence acting as transdominant-negative mutants of CIITA function, was tested. All the mutants described above in the previous Examples were tested for transdominant-negative activities. The mutants exhibiting transdominant-negative properties are shown in the Table below. The experiment consists of the co-transfection of the pDRACAT300 reporter together with CIITA and empty vector, or a mutant form of CIITA. A titration of wild-type vs. mutant CIITA constructs established that a 1:1 ratio was sufficient to reveal several transdominant mutants (data not shown). Three mutants greatly reduced the function of wild-type CIITA, with maximal reduction of wild-type CIITA function by approximately 96%. The effective transdominant mutants are: the CIITA(Δ132–301) mutant which has the proline/serine/threonine-rich domain deleted; the CIITA(1–1017) mutant, which has the C-terminus from residues 1018–1130 deleted; and the CIITA-GTP2(ΔDAYG) mutant, which has the G3 motif deleted.

Transdominant Repression of DRA-CAT Expression by CIITA Mutants

| | 1 | 2 | 3 | 4 |
|---|---|---|---|---|
| ddDRCAT | + | + | + | + |
| pCDNA3 | + | – | – | – |
| FLAG.CIITA | + | + | + | + |
| Mutants | – | CIITA (Δ132–301) | CIITA (1–1017) | CIITA-GTP2(ΔDAYG) |
| Percentage Inhibition[1] | – | 93.9 | 91.9 | 82.4 |

[1]Percentage Inhibition of wild-type FLAG.CIITA-induced DRA-CAT Expression = FLAG.CIITA Activity-Mutant CIITA Activity/FLAG.CIITA Activity × 100%

The identification of transdominant negative mutants of CIITA has both practical and molecular implications. The mutants may be efficient in suppressing Class II MHC promoter function and gene expression in an in vivo condition. For example, it may be possible to produce animals bearing such transdominant-negative CIITA molecules, and utilize these for transplant purposes. It is of some interest that the deletion/mutation of three specific domains resulted in potent and highly efficient transdominant-negative functions. Presumably, what remains unmutated in these molecules is sufficient to block the function of wild-type CIITA, perhaps by interceding certain intracellular signals. The fact that the transdominant-negative function is observed at a 1:1 ratio of wild-type:mutant CIITA suggests that the mutant form is more efficient at interceding such putative signals or functions.

The foregoing Examples are illustrative of the present invention, and are not to be construed as limiting thereof. The invention is defined by the following claims, with equivalents of the claims to be included therein.

That which is claimed:

1. A human mutant class II transactivator (CIITA) protein, not naturally occurring, selected from the group consisting of mutant proteins encoded by CIITA(Δ132–301), CIITA(Δ132–212), CIITA(Δ209–301), CIITA-GTP1(ΔGK), CIITA-GTP1(K→E), CIITA-GTP2(ΔDAYG), CIITA-GTP-3(ΔSKAD), CIITA(1–931), CIITA(1–949), CIITA(1–1017), CIITA(1–1059), and CIITA(1–1089).

* * * * *